(12) United States Patent
Gupta et al.

(10) Patent No.: US 8,350,045 B2
(45) Date of Patent: Jan. 8, 2013

(54) PROCESS FOR PREPARATION OF E-ISOMER OF 1-(4-METHYLPHENYL)-1-(2-PYRIDYL)-3-PYRROLIDINO PROP-1-ENE AND ACID ADDITION SALTS THEREOF

(75) Inventors: Rajender Pershad Gupta, Bangalore (IN); Veerabhadra Swamy Hiremath, Bangalore (IN); Raghavendra Arekal Vasanna, Bangalore (IN); Vasantha Gowda Nekkilar, Bangalore (IN)

(73) Assignee: Hikal Limited (IN)

( * ) Notice: Subject to any disclaimer, the term of this patent is extended or adjusted under 35 U.S.C. 154(b) by 206 days.

(21) Appl. No.: 12/808,516

(22) PCT Filed: Dec. 16, 2008

(86) PCT No.: PCT/IN2008/000839
§ 371 (c)(1),
(2), (4) Date: Sep. 1, 2010

(87) PCT Pub. No.: WO2009/084035
PCT Pub. Date: Jul. 9, 2009

(65) Prior Publication Data
US 2011/0046384 A1    Feb. 24, 2011

(30) Foreign Application Priority Data

Dec. 17, 2007 (IN) .......................... 3003/CHE/2007

(51) Int. Cl.
*C07D 401/02* (2006.01)
(52) U.S. Cl. .................................... 546/276.4
(58) Field of Classification Search ............. 546/276.4
See application file for complete search history.

(56) References Cited

U.S. PATENT DOCUMENTS 2,712,023 A * 6/1955 Adamson ................... 546/276.4

OTHER PUBLICATIONS

Casy et al., "Analogues of triprolidine: structural influences upon antihistamine activity" *J. Pharm. and Pharmacol.* 44:791-795 (1992).
International Preliminary Report on Patentability, PCT/IN2008/000839, dated Jun. 22, 2010.
International Search Report, PCT/IN2008/000839, dated Jul. 9, 2009.
Written Opinion of the International Searching Authority, PCT/IN2008/000839, dated Jun. 17, 2010.

* cited by examiner

*Primary Examiner* — Patricia Morris
(74) *Attorney, Agent, or Firm* — Choate Hall & Stewart LLP; Andrea L. C. Robidoux; Xiaodong Li

(57) ABSTRACT

A process for preparation of E-isomer of 1-(4-methylphenyl)-1-(2-pyridyl)-3-pyrrolidinoprop-1-ene of Formula-I, and acid addition salts thereof, said process comprising; dehydrating 1-(4-methylphenyl)-1-(2-pyridyl)-3-pyrrolidinopropan-1-ol of Formula III followed by adding a base solution to obtain a mixture of E and Z isomers of 1-(4-methylphenyl)-1-(2-pyridyl)-3-pyrrolidinoprop-1-ene, and washing said mixture of E and Z isomers of 1-(4-methylphenyl)-1-(2-pyridyl)-3-pyrrolidinoprop-1-ene with water to dissolve Z isomer and to obtain E-isomer of 1-(4-methylphenyl)-1-(2-pyridyl)-3-pyrrolidinoprop-1-ene of Formula I, which is substantially free from Z isomer.

(I)

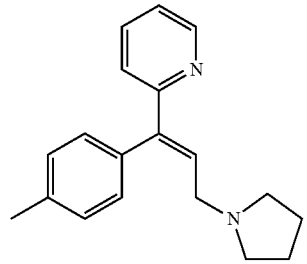

13 Claims, No Drawings

PROCESS FOR PREPARATION OF E-ISOMER OF 1-(4-METHYLPHENYL)-1-(2-PYRIDYL)-3-PYRROLIDINO PROP-1-ENE AND ACID ADDITION SALTS THEREOF

TECHNICAL FIELD

The present invention provides a process for preparation of E-isomer of 1-(4-methylphenyl)-1-(2-pyridyl)-3-pyrrolidino prop-1-ene (Triprolidine) (Formula I), which is substantially free from corresponding Z-isomer and acid addition salts thereof.

BACKGROUND AND PRIOR ART

E-isomer of 1-(4-methylphenyl)-1-(2-pyridyl)-3-pyrrolidinoprop-1-ene (Formula I) exhibits anti-histamine activity.

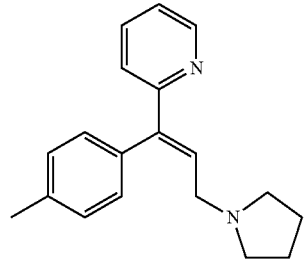

Formula I

U.S. Pat. No. 2,712,023 disclose a process for preparing E-isomer of 1-(4-methylphenyl)-1-(2-pyridyl)-3-pyrrolidinoprop-1-ene (Formula I) from 1-(4-methylphenyl)-1-(2-pyridyl)-3-pyrrolidinopropan-1-ol (Formula III). 4-methyl-ω-pyrrolidinopropiophenone required for the preparation of the carbinol is prepared by Mannich reaction from 4-methyl acetophenone and pyrrolidine. 1-(4-Methylphenyl)-1-(2-pyridyl)-3-pyrrolidinopropan-1-ol is heated at 165° C. for 10 minutes with aqueous sulphuric acid (85%, 20 cc). The solution is then poured on to crushed ice, basified with excess ammonia solution and the liberated oil is extracted with light petroleum (B.P. 60-80°). The extract is dried over anhydrous sodium sulphate and the solvent is evaporated to leave amber syrup consisting of the E and Z isomers of 1-(4-methylphenyl)-1-(2-pyridyl)-3-pyrrolidinoprop-1-ene. The mixture of isomers is passed onto a column of sulphonated cross-linked polystyrene to isolate the isomers. The isomers are converted to their oxalates and recrystallisation of trans isomer oxalate from methanol gave pure oxalate of trans isomer of 1-(4-methylphenyl)-1-(2-pyridyl)-3-pyrrolidinoprop-1-ene.

U.S. Pat. No. 2,712,023 disclose that separation of the isomers can be accomplished by a number of methods, e.g., fractional crystallization, chromatographic method or separation by Base Exchange Chromatography.

Normally, when separation methods such as column chromatography are used in order to separate compounds from a mixture, it is observed that these methods are associated with the use of large volumes of solvents resulting in a process of longer duration and the subsequent purifications steps for the removal of excess solvents.

Indian Patent Application No. 992/CHE/2006 discloses a process for preparation of E-isomer of 1-(4-methylphenyl)-1-(2-pyridyl)-3-pyrrolidinoprop-1-ene by reacting 2-(1-pyrrolidino)ethyl triphenyl phosphonium bromide with 2-(p-toluoyl)pyridine in presence of an aprotic solvent and a base followed by isomerization in presence of an acid catalyst.

OBJECTS OF THE PRESENT INVENTION

A primary object of the present invention is to provide a process for preparation of substantially pure E-isomer of 1-(4-methylphenyl)-1-(2-pyridyl)-3-pyrrolidinoprop-1-ene (Formula I), which is substantially free from corresponding Z-isomer.

Another object of the present invention is to provide a process for preparation of substantially pure E-isomer of 1-(4-methylphenyl)-1-(2-pyridyl)-3-pyrrolidinoprop-1-ene (Formula I) without using an ion exchange column chromatography technique or fractional crystallization of salts.

It is an object of the present invention to provide a process for preparation of substantially pure acid addition salt of E-isomer of 1-(4-methylphenyl)-1-(2-pyridyl)-3-pyrrolidinoprop-1-ene (Formula I).

SUMMARY OF THE INVENTION

The present invention relates to a process for preparation of E-isomer of 1-(4-methylphenyl)-1-(2-pyridyl)-3-pyrrolidinoprop-1-ene of Formula I, which is substantially free from corresponding Z-isomer

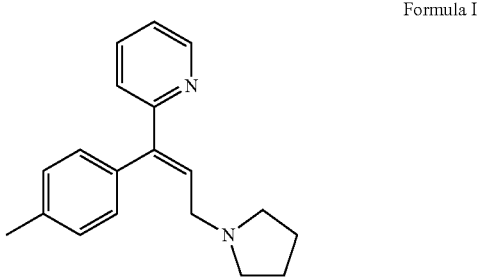 [SMILES: Cc1ccc(/C(=C\CN2CCCC2)c2ccccn2)cc1]

Formula I said process comprising; adding 1-(4-methylphenyl)-1-(2-pyridyl)-3-pyrrolidinopropan-1-ol (Formula III), to a solution of about 90% concentrated sulphuric acid, at a temperature in the range of 25 to 110° C. for a period of about 1 to 6 hours to obtain a reaction mass and cooling said reaction mass to obtain a solution of 1-(4-methylphenyl)-1-(2-pyridyl)-3-pyrrolidinoprop-1-ene sulphate, adding a base solution to said solution of 1-(4-methylphenyl)-1-(2-pyridyl)-3-pyrrolidinoprop-1-ene sulphate to precipitate a mixture of E and Z isomers of 1-(4-methylphenyl)-1-(2-pyridyl)-3-pyrrolidinoprop-1-ene, and washing the said mixture of E and Z isomers of 1-(4-methylphenyl)-1-(2-pyridyl)-3-pyrrolidinoprop-1-ene with water to dissolve the Z-isomer and to obtain E-isomer of 1-(4-methylphenyl)-1-(2-pyridyl)-3-pyrrolidinoprop-1-ene (Formula I), which is free from the corresponding Z isomer thus avoiding use of ion exchange column chromatography technique or conversion to oxalate salt followed by fractional crystallization. The present invention also provides a process for the preparation of acid addition salts of E-isomer of 1-(4-methylphenyl)-1-(2-pyridyl)-3-pyrrolidinoprop-1-ene (Formula I), by dissolving E-isomer of 1-(4-methylphenyl)-1-(2-pyridyl)-3-pyrrolidinoprop-1-ene (Formula I) in an aromatic solvent and shaking with corresponding acid.

DETAILED DESCRIPTION OF THE INVENTION

Accordingly, the present invention provides process for preparation of E-isomer of 1-(4-methylphenyl)-1-(2-pyridyl)-3-pyrrolidinoprop-1-ene of Formula-I, which is substantially free from corresponding Z-isomer Formula I

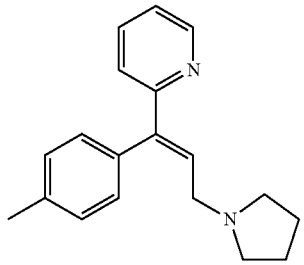

said process comprising; reacting 4-methylacetophenone, pyrrolidine and paraformaldehyde in n-butanol, concentrated hydrochloric acid and aqueous ammonia to obtain 4'-methyl-3-pyrrolidino-propiophenone of Formula II, Formula II

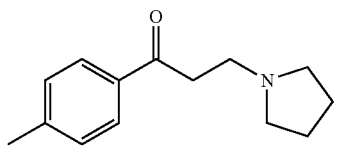

reacting 4'-methyl-3-pyrrolidino-propiophenone of Formula II in toluene with 2-bromopyridine and solution of n-butyllithium in a hydrocarbon solvent such as hexane to obtain 1-(4-methylphenyl)-1-(2-pyridyl)-3-pyrrolidinopropan-1-ol of Formula III, Formula III

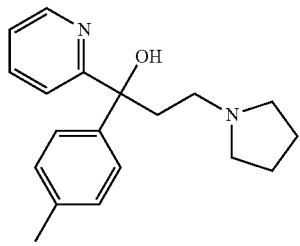

adding 1-(4-methylphenyl)-1-(2-pyridyl)-3-pyrrolidinopropan-1-ol of Formula III to a solution of about 90% concentrated sulphuric acid, at a temperature in the range of 25 to 110° C. for a period of about 1 to 6 hours to perform dehydration 1-(4-methylphenyl)-1-(2-pyridyl)-3-pyrrolidinopropan-1-ol (Formula III) to obtain a reaction mass and cooling said reaction mass to obtain a solution of 1-(4-methylphenyl)-1-(2-pyridyl)-3-pyrrolidinoprop-1-ene sulphate, adding a base solution to said solution of 1-(4-methylphenyl)-1-(2-pyridyl)-3-pyrrolidinoprop-1-ene sulphate to obtain >92% of E-isomer along with <8% Z-isomer of 1-(4-methylphenyl)-1-(2-pyridyl)-3-pyrrolidinoprop-1-ene, and washing the said mixture of E and Z isomers of 1-(4-methylphenyl)-1-(2-pyridyl)-3-pyrrolidinoprop-1-ene with water to dissolve Z-isomer and to obtain E-isomer of 1-(4-methylphenyl)-1-(2-pyridyl)-3-pyrrolidinoprop-1-ene (Formula I).

An embodiment of the present invention, wherein the reaction between 1-(4-methylphenyl)-1-(2-pyridyl)-3-pyrrolidinopropan-1-ol (Formula III) and the solution of 90% concentrated sulphuric acid is performed at a temperature of about 40-110° C., preferably at about 100° C. to 110° C.

Another embodiment of the present invention, wherein the reaction between 1-(4-methylphenyl)-1-(2-pyridyl)-3-pyrrolidinopropan-1-ol (Formula III) and the solution of 90% concentrated sulphuric acid is carried out for a period of time about 4 hours.

Yet another embodiment of the present invention, wherein dehydration of 1-(4-methylphenyl)-1-(2-pyridyl)-3-pyrrolidinopropan-1-ol (Formula III) is performed in presence of a reagent selected from acetic anhydride, HCl and p-toluenesulphonic acid.

Still yet another embodiment of the present invention, wherein the base solution is an alkali metal hydroxide or an alkaline earth metal hydroxide or an aqueous ammonia or a quaternary ammonium hydroxide.

Further an embodiment of the present invention, wherein the alkali metal hydroxide is sodium hydroxide and the alkaline earth metal hydroxide is potassium hydroxide.

The steps of the process to prepare E-isomer of 1-(4-methylphenyl)-1-(2-pyridyl)-3-pyrrolidino prop-1-ene (Formula I) are also depicted in the form of the following reaction scheme.

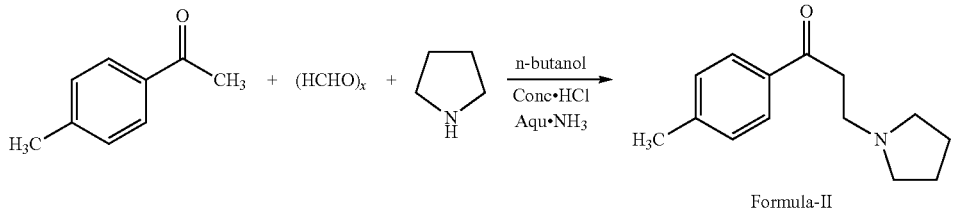

Formula-II

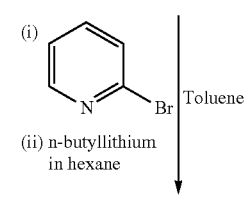

(i)

(ii) n-butyllithium in hexane

Toluene

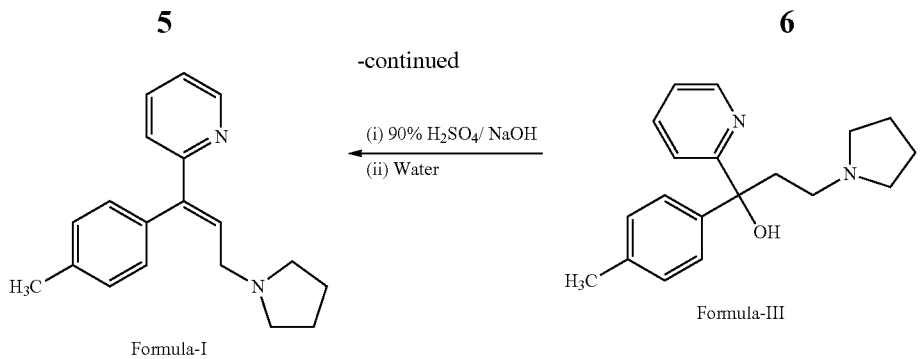

Formula-I ⇌ Formula-III
(i) 90% H₂SO₄/ NaOH
(ii) Water

It is also observed that when 90% concentrated sulphuric acid is used for the dehydration of 1-(4-methylphenyl)-1-(2-pyridyl)-3-pyrrolidinopropan-1-ol (Formula III), a substantially pure E-isomer of 1-(4-methylphenyl)-1-(2-pyridyl)-3-pyrrolidino prop-1-ene (Formula I) is obtained. However, when the concentration of sulphuric acid is lesser than 90%, the formation of more Z isomer 1-(4-methylphenyl)-1-(2-pyridyl)-3-pyrrolidino prop-1-ene is observed.

Process Steps for Separation of Substantially Pure E-isomer of 1-(4-methylphenyl)-1-(2-pyridyl)-3-pyrrolidinoprop-1-ene (Formula I)

The compound 1-(4-methylphenyl)-1-(2-pyridyl)-3-pyrrolidinoprop-1-ene, which is obtained as a result of basification of 1-(4-methylphenyl)-1-(2-pyridyl)-3-pyrrolidinoprop-1-ene sulphate, is a mixture of E and Z isomers of 1-(4-methylphenyl)-1-(2-pyridyl)-3-pyrrolidinoprop-1-ene.

In order to separate E-isomer of 1-(4-methylphenyl)-1-(2-pyridyl)-3-pyrrolidinoprop-1-ene (Formula I), applicant has undertaken the separation process, wherein the use of organic solvents is avoided.

Therefore, in the separation steps of the present invention water is used as a solvent, to wash the mixture of E and Z isomers of 1-(4-methylphenyl)-1-(2-pyridyl)-3-pyrrolidinoprop-1-ene, to dissolve Z isomer thereby separating E-isomer of 1-(4-methylphenyl)-1-(2-pyridyl)-3-pyrrolidinoprop-1-ene (Formula I), without resorting to the use of organic solvents.

Process Steps for Preparation of Acid Addition Salts of E-isomer of 1-(4-methylphenyl)-1-(2-pyridyl)-3-pyrrolidinoprop-1-ene (Formula I)

The present disclosure also provides a process for preparing acid addition salts of E-isomer of 1-(4-methylphenyl)-1-(2-pyridyl)-3-pyrrolidinoprop-1-ene (Formula I). More particularly, as an exemplary embodiment, a process for the preparation E-isomer of 1-(4-methylphenyl)-1-(2-pyridyl)-3-pyrrolidinoprop-1-ene hydrochloride monohydrate (Formula IV).

The process steps for the preparation of E-isomer of 1-(4-methylphenyl)-1-(2-pyridyl)-3-pyrrolidinoprop-1-ene hydrochloride monohydrate (Formula IV) are described below:

E-isomer of 1-(4-methylphenyl)-1-(2-pyridyl)-3-pyrrolidinoprop-1-ene (Formula I) is dissolved in an aromatic solvent such as toluene, xylene, chlorobenzene, dichlorobenzene, and mesitylene, preferably toluene to obtain a solution of E-isomer of 1-(4-methylphenyl)-1-(2-pyridyl)-3-pyrrolidinoprop-1-ene (Formula I). The solution of E-isomer of 1-(4-methylphenyl)-1-(2-pyridyl)-3-pyrrolidinoprop-1-ene (Formula I) is treated with charcoal to obtain a filtrate of E-isomer of 1-(4-methylphenyl)-1-(2-pyridyl)-3-pyrrolidinoprop-1-ene (Formula I). A corresponding acid is added to the filtrate of E-isomer of 1-(4-methylphenyl)-1-(2-pyridyl)-3-pyrrolidinoprop-1-ene (Formula I) to obtain an acid addition salt of E-isomer of 1-(4-methylphenyl)-1-(2-pyridyl)-3-pyrrolidinoprop-1-ene (Formula I), and it is recrystallized from acetone to obtain substantially pure acid addition salt of E-isomer of 1-(4-methylphenyl)-1-(2-pyridyl)-3-pyrrolidinoprop-1-ene.

The acid addition salts of E-isomer of 1-(4-methylphenyl)-1-(2-pyridyl)-3-pyrrolidinoprop-1-ene (Formula I) are prepared by using an acid in the presence of an aromatic solvent. The acid that can be used in the present process can be selected from HCl, or aliphatic dicarboxylic acid such as Oxalic acid.

In the present invention, as an exemplary embodiment, E-isomer of 1-(4-methylphenyl)-1-(2-pyridyl)-3-pyrrolidinoprop-1-ene hydrochloride monohydrate (Formula IV) is prepared in the following manner.

The schematic reaction steps of the process to prepare E-isomer of 1-(4-methylphenyl)-1-(2-pyridyl)-3-pyrrolidinoprop-1-ene hydrochloride monohydrate (Formula IV) are shown below:

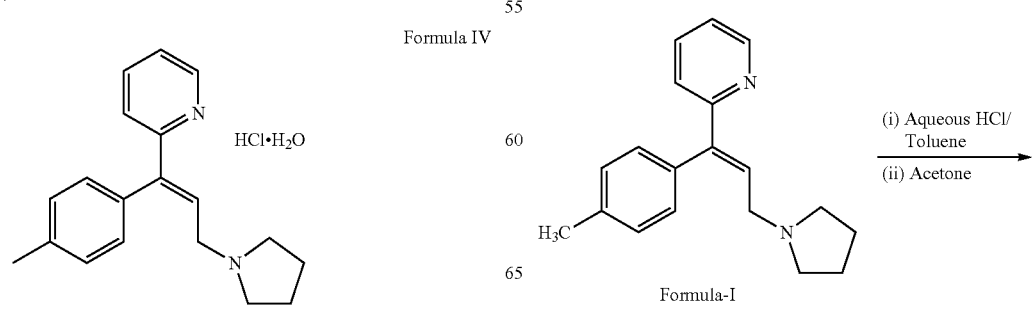

Formula IV (HCl·H₂O) ← Formula-I
(i) Aqueous HCl/ Toluene
(ii) Acetone

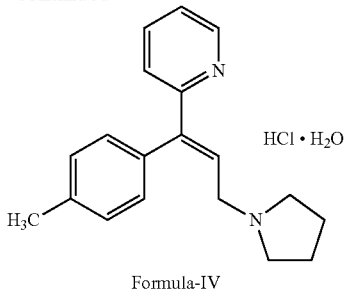

Formula-IV

In the present process hydrochloride salt of E-isomer of 1-(4-methylphenyl)-1-(2-pyridyl)-3-pyrrolidinoprop-1-ene (Formula I) is prepared by shaking E-isomer of 1-(4-methylphenyl)-1-(2-pyridyl)-3-pyrrolidinoprop-1-ene (Formula I) in toluene with aqueous HCl. The aqueous filtrate containing Z isomer is extracted with an aromatic solvent such as toluene and concentrated to dryness. The residue containing rich in Z isomer is again converted to E-isomer by treatment with 90% $H_2SO_4$ in a similar manner as has been done for dehydration of 1-(4-methylphenyl)-1-(2-pyridyl)-3-pyrrolidinopropan-1-ol (Formula III).

The process steps of the present invention are described in the following examples, which are illustrative in nature only and should not be construed as limiting the scope of the invention in any manner.

EXAMPLE 1

Step 1: Preparation of 4'-methyl-3-pyrrolidino propiophenone (Formula II)

The 4'-methyl-3-pyrrolidino propiophenone required as the starting material for the preparation of triprolidine alcohol is prepared by Mannich reaction from 4-methylacetophenone, pyrrolidine and paraformaldehyde. 900 ml of n-butanol, 150 g of pyrrolidine, 318 g of HCl (29%), 291 g of 4-methylacetophenone and 126 g of para-formaldehyde are charged in to a 4-neck R.B. flask. The reaction mass is heated to 85° C. to 90° C. and the same temperature is maintained for 12 to 14 hours. After completion of the reaction, n-butanol along with water is completely distilled off under vacuum and then 1.2 litres of toluene is added to reaction mass under stirring at hot condition. The reaction mass is cooled to 10-15° C. and same temperature maintained for 30-45 minutes. The solid mass is filtered and Mannich hydrochloride (85%) is obtained with >98% HPLC purity. To 450 ml of water, solid mass is added and stirred for 15 to 30 minutes for complete dissolution, ammonia is added slowly and temperature is kept at 10°-20° C. for 1 hour. The solid mass is filtered and dried under suction for 1 hour to obtain 347 g of 4'-methyl-3-pyrrolidinopropiophenone (76%) with >98% HPLC purity with m.p. in the range of 42-45° C.

Step 2: Preparation of 1-(4-methylphenyl)-1-(2-pyridyl)-3-pyrrolidinopropan-1-ol (Formula III)

400 ml of toluene is charged into a round-bottom flask, which is cooled to −40° C. and then solution of n-butyllithium (76.6 g) in hexane is added and the temperature of the reaction mixture is maintained at −40° to −50° C. 2-Bromopyridine (189.2 g) is then added to the reaction mixture and the temperature is maintained at −65° to −55° C. for 35 to 45 minutes. 200 g of 4'-methyl-3-pyrrolidinopropiophenone in 200 ml of toluene is added to the reaction mixture in the R.B. flask. The reaction mass is stirred at −65° to −55° C. for 2 hours and it is further stirred for 1 hour at −40° to −50° C. The reaction mass is quenched in ice water and HCl is added slowly at 10° to 20° C. to get a clear solution. The aqueous layer is separated and it is added slowly to NaOH in the R.B. flask at 15° C.-20° C. The reaction mass is stirred for half an hour and the precipitated solid is filtered off. The solid is transferred into a round-bottom flask and then 500 ml of methanol is added. The reaction mass is refluxed at 60° C. for half an hour and the mass is cooled to 10°-20° C. The solid mass is filtered and dried under suction for one hour. On drying the solid compound at 70°-80° C. for 4 hours, 1-(4-methylphenyl)-1-(2-pyridyl)-3-pyrrolidinopropan-1-ol (220 g, 80.5% yield) with 99.3% HPLC purity is obtained whose melting point is in the range of 115°-119° C.

Step 3: Preparation of E-isomer of 1-(4-methylphenyl)-1-(2-pyridyl)-3-pyrrolidino prop-1-ene (Formula I)

45 ml of demineralized water is charged into a round-bottomed flask kept at 25° to 30° C. and then slowly 405 ml of 90% Conc. $H_2SO_4$ is added and the temperature is raised to 40° C.-60° C. under stirring. Slowly 150 g of 1-(4-methylphenyl)-1-(2-pyridyl)-3-pyrrolidinopropan-1-ol is charged and the temperature is maintained at 85° C. under stirring. The reaction mass is heated to 100-105° C. and the temperature is maintained for 4 hours under stirring. After completion of the reaction, the reaction mass is cooled to 25°-30° C. and then poured into ice cold water (3 litre) at 5-10° C. under stirring over a period of one hour. 50% NaOH solution (w/w) is added slowly to the reaction mixture while maintaining the temperature at 5° to 20° C. over a period of 2 hours and the contents are stirred for an hour at 25° to 30° C. The reaction mixture is filtered under suction to obtain 161 g wet triprolidine base comprising >92% E-isomer along with <8% Z-isomer. 1.5 litres of demineralized water and 161 g wet triprolidine base are charged into a round-bottom flask at 25° to 30° C. and the contents are stirred for 3 hours by maintaining the same temperature. The contents are filtered and dried under suction for 2 hours. The process is repeated thrice to obtain 1-(4-methylphenyl)-1-(2-pyridyl)-3-pyrrolidino prop-1-ene (115 g, 82%) comprising of >98% E-isomer along with <2% of Z-isomer.

In the above-stated process steps, triprolidine alcohol is prepared by Mannich Reaction from 4-methylacetophenone, pyrrolidine and paraformaldehyde followed by reaction of 4'-methyl-3-pyrrolidinopropiophenone with 2-bromopyridine and n-butyllithium. However, other known suitable processes for the preparation of triprolidine alcohol can also be used.

EXAMPLE 2

Preparation of E-isomer of 1-(4-methylphenyl)-1-(2-pyridyl)-3-pyrrolidino prop-1-ene (Formula I)

15 ml of demineralized water is charged into a round-bottomed flask kept at 25° to 30° C. and then slowly 243 ml of 90% Conc. $H_2SO_4$ is added and the temperature is raised to 10° C.-20° C. under stirring. Slowly 50 g of 1-(4-methylphenyl)-1-(2-pyridyl)-3-pyrrolidinopropan-1-ol is charged and the temperature is maintained at 20° C. under stirring. The reaction mass is heated to 100-105° C. and the temperature is maintained for 4 hours under stirring. After completion of the reaction, the reaction mass is cooled to 25°-30° C., and then poured into ice cold water (1 litre) at 5-10° C. under stirring over a period of an hour. 50% NaOH solution (w/w) is added slowly to the reaction mixture by maintaining the temperature at 5° to 20° C. over a period of 2 hours and the contents are stirred for an hour at 25° to 30° C. The reaction mixture is filtered under suction to obtain 51.3 g of wet triprolidine base comprising >92% E-isomer along with <8% Z-isomer. 500 ml of demineralized water and 51.3 g of wet triprolidine base are charged into a round-bottom flask at 25° to 30° C. and the contents are stirred for 3 hours by maintaining the same temperature. The contents are filtered and dried under suction for 2 hours. The process is repeated thrice to obtain 1-(4-methylphenyl)-1-(2-pyridyl)-3-pyrrolidino prop-1-ene (38 g, 81.2%) consisting of >98% E isomer along with <2% Z-isomer.

EXAMPLE 3

Preparation of E-isomer of 1-(4-methylphenyl)-1-(2-pyridyl)-3-pyrrolidino prop-1-ene (Formula I)

60 ml of demineralized water is charged into a round-bottomed flask kept at 25° to 30° C. and then slowly 540 ml of 90% Conc. $H_2SO_4$ is added and the temperature is raised to 40° C.-60° C. under stirring. Slowly 200 g of 1-(4-methylphenyl)-1-(2-pyridyl)-3-pyrrolidinopropan-1-ol is charged and the temperature is maintained at 85° C. under stirring. The reaction mass is heated to 100-105° C. and the temperature is maintained for 4 hours under stirring. After completion of the reaction, the reaction mass is cooled to 25°-30° C. and then poured into ice cold water (4 litre) at 5-10° C. under stirring over a period of an hour. 50% NaOH solution (w/w) is added slowly to the reaction mixture by maintaining the temperature at 5° to 20° C. over a period of 2 hours and the contents are stirred for an hour at 25° to 30° C. The reaction mixture is filtered under suction to obtain 286 g of wet triprolidine base comprising >92% E-isomer along with <8% Z-isomer. 2 litres of demineralized water and 286 g of wet triprolidine base are charged into a round-bottom flask at 25° to 30° C. and the contents are stirred for 3 hours by maintaining the same temperature. The contents are filtered and dried under suction for 2 hours. The process is repeated thrice to obtain 1-(4-methylphenyl)-1-(2-pyridyl)-3-pyrrolidino prop-1-ene (150 g, 80%) consisting of >98% E isomer along with <2% Z-isomer.

EXAMPLE 4

Preparation of E-isomer of 1-(4-methylphenyl)-1-(2-pyridyl)-3-pyrrolidino prop-1-ene hydrochloride monohydrate (hydrochloride salt of E-isomer of 1-(4-methylphenyl)-1-(2-pyridyl)-3-pyrrolidino prop-1-ene) (Formula IV)

378 ml of toluene is added to 126 g of E-isomer of 1-(4-methylphenyl)-1-(2-pyridyl)-3-pyrrolidino prop-1-ene under stirring over a period of 30 minutes at 25-30° C. and then 5 g of charcoal is added under stirring and continued the stirring for an hour at 25-30° C. The reaction mass is filtered through hyflo, and then 34.57 ml of aqueous HCl is added to clear filtrate under stirring for 30 minutes at 20-25° C. The reaction mass is filtered to obtain 142 g of wet hydrochloride salt of E-isomer of 1-(4-methylphenyl)-1-(2-pyridyl)-3-pyrrolidino prop-1-ene. 142 g of wet hydrochloride salt of E-isomer of 1-(4-methylphenyl)-1-(2-pyridyl)-3-pyrrolidino prop-1-ene is charged into one litre round-bottom flask followed by 500 ml of acetone. The reaction mass is heated at reflux to dissolve the reaction mixture completely. Charcoal is added to the reaction mass and the contents are refluxed for half an hour and filtered at hot condition. The filtrate is cooled to room temperature first and to 0° C. The mass is filtered and dried to obtain 90 g (53%) of E-isomer of 1-(4-methylphenyl)-1-(2-pyridyl)-3-pyrrolidino prop-1-ene hydrochloride monohydrate (Formula IV) with 99.79% HPLC purity which melts in the range from 116°-118° C.

ADVANTAGES

1. By using the process of the present invention purity of E-isomer of 1-(4-methylphenyl)-1-(2-pyridyl)-3-pyrrolidinoprop-1-ene (Formula I) is >98%.
2. The process of the present invention does not adopt recrystallisation steps to obtain the required E isomer.
3. The present invention provides a process wherein Z isomer is removed from E isomer by washing the mixture of isomers with water since Z isomer is preferentially soluble in water. Repeated water washing enhances the required E isomer and brings down the Z isomer to less than 2%.

We claim:
1. A process for preparation of E-isomer of 1-(4-methylphenyl)-1-(2-pyridyl)-3-pyrrolidinoprop-1-ene of Formula I or its acid addition salts thereof, which are substantially free from corresponding Z-isomer

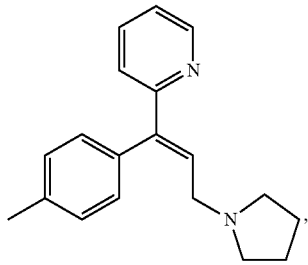

Formula I said process comprising:
a. adding 1-(4-methylphenyl)-1-(2-pyridyl)-3-pyrrolidinopropan-1-ol to a solution of at least 90% concentrated sulphuric acid, at a temperature in the range of 25 to 110° C. for a period of 1 to 6 hours to obtain a solution of 1-(4-methylphenyl)-1-(2-pyridyl)-3-pyrrolidinoprop-1-ene sulphate,
b. adding a base solution to said solution of 1-(4-methylphenyl)-1-(2-pyridyl)-3-pyrrolidinoprop-1-ene sulphate to obtain a mixture of E and Z isomers of 1-(4-methylphenyl)-1-(2-pyridyl)-3-pyrrolidinoprop-1-ene, and
c. washing said mixture of E and Z isomers of 1-(4-methylphenyl)-1-(2-pyridyl)-3-pyrrolidinoprop-1-ene with water to dissolve Z isomer and to obtain E-isomer of 1-(4-methylphenyl)-1-(2-pyridyl)-3-pyrrolidinoprop-1-ene of Formula I, which is substantially free from Z isomer.
2. The process as claimed in claim 1, wherein the reaction between 1-(4-methylphenyl)-1-(2-pyridyl)-3-pyrrolidinopropan-1-ol and the solution of sulphuric acid is performed at a temperature of 40-110° C.
3. The process as claimed in claim 1, wherein the reaction between 1-(4-methylphenyl)-1-(2-pyridyl)-3-pyrrolidinopropan-1-ol and the solution of sulphuric acid is carried out for a period of time 4 hours.

4. The process as claimed in claim 1, wherein the base solution is an alkali metal hydroxide or an alkaline earth metal hydroxide or aqueous ammonia or quaternary ammonium hydroxide.

5. The process as claimed in claim 4, wherein the alkali metal hydroxide is sodium hydroxide and the alkaline earth metal hydroxide is potassium hydroxide.

6. The process as claimed in claim 1, wherein an acid addition salt of E-isomer of 1-(4-methylphenyl)-1-(2-pyridyl)-3-pyrrolidinoprop-1-ene is prepared by reacting E-isomer of 1-(4-methylphenyl)-1-(2-pyridyl)-3-pyrrolidinoprop-1-ene of Formula I with a corresponding acid.

7. The process as claimed in claim 6, where the acid is hydrochloric acid and the salt is E-isomer of 1-(4-methylphenyl)-1-(2-pyridyl)-3-pyrrolidinoprop-1-ene hydrochloride monohydrate.

8. The process as claimed in claim 6 or 7, wherein E-isomer of 1-(4-methylphenyl)-1-(2-pyridyl)-3-pyrrolidinoprop-1-ene hydrochloride monohydrate is prepared by shaking E-isomer of 1-(4-methylphenyl)-1-(2-pyridyl)-3-pyrrolidinoprop-1-ene of Formula-I in an aromatic solvent with aqueous hydrochloric acid.

9. The process as claimed in claim 7, wherein the strength of hydrochloric acid is 25 to 35%.

10. The process as claimed in claim 8, wherein the aromatic solvent is selected from the group consisting of toluene, xylene, chlorobenzene, dichlorobenzene, and mesitylene.

11. The process as claimed in claim 1, wherein 1-(4-methylphenyl)-1-(2-pyridyl)-3-pyrrolidinopropan-1-ol is added to a solution of 90% sulfuric acid.

12. The process as claimed in claim 1, wherein the reaction between 1-(4-methylphenyl)-1-(2-pyridyl)-3-pyrrolidinopropan-1-ol and the solution of sulphuric acid is performed at a temperature of 100° C. to 110° C.

13. The process as claimed in claim 8, wherein the aromatic solvent is toluene.

* * * * *